(12) United States Patent
Fujimori et al.

(10) Patent No.: US 7,884,239 B2
(45) Date of Patent: Feb. 8, 2011

(54) CATALYST FOR PRODUCING α,β-UNSATURATED CARBOXYLIC ACID AND METHOD FOR PREPARATION THEREOF, AND METHOD FOR PRODUCING α,β-UNSATURATED CARBOXYLIC ACID

(75) Inventors: Yuji Fujimori, Otake (JP); Wataru Ninomiya, Otake (JP); Akio Takeda, Otake (JP); Mai Kojima, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 12/388,917

(22) Filed: Feb. 19, 2009

(65) Prior Publication Data

US 2009/0156860 A1 Jun. 18, 2009

Related U.S. Application Data

(62) Division of application No. 10/588,973, filed as application No. PCT/JP2005/001804 on Feb. 8, 2005, now abandoned.

(30) Foreign Application Priority Data

| Feb. 10, 2004 | (JP) | 2004-033256 |
| Feb. 10, 2004 | (JP) | 2004-033276 |
| Aug. 10, 2004 | (JP) | 2004-233287 |

(51) Int. Cl.
C07C 51/235 (2006.01)

(52) U.S. Cl. .................................................... 562/532

(58) Field of Classification Search .................. 562/532, 562/600
See application file for complete search history.

(56) References Cited

U.S. PATENT DOCUMENTS

| 3,969,274 | A | | 7/1976 | Frampton |
| 4,435,598 | A | * | 3/1984 | Hinnenkamp ............... 562/546 |
| 5,082,819 | A | | 1/1992 | Boeck et al. |
| 5,153,162 | A | | 10/1992 | Kurimoto et al. |
| 7,446,223 | B2 | | 11/2008 | Ninomiya et al. |
| 2003/0157011 | A1 | | 8/2003 | Mori |
| 2006/0068989 | A1 | | 3/2006 | Ninomiya et al. |
| 2008/0025900 | A1 | | 1/2008 | Mori |

FOREIGN PATENT DOCUMENTS

| CN | 1315228 A | 10/2001 |
| CN | 1421388 | 6/2003 |
| CN | 1697696 | 11/2005 |
| JP | 51 1389 | 1/1976 |
| JP | 56 59722 | 5/1981 |
| JP | 60 139341 | 7/1985 |
| JP | 60 139643 | 7/1985 |
| JP | 60 155148 | 8/1985 |
| JP | 3 86242 | 4/1991 |
| JP | 3 109946 | 5/1991 |
| JP | 2001 17222 | 6/2001 |
| WO | 02 083299 | 10/2002 |

* cited by examiner

*Primary Examiner*—Taylor Victor Oh
(74) *Attorney, Agent, or Firm*—Oblon, Spivak, McClelland, Maier & Neustadt, L.L.P.

(57) ABSTRACT

The object of the present invention is to provide a catalyst which can produce an α,β-unsaturated carboxylic acid through liquid-phase oxidation of an olefin or an α,β-unsaturated aldehyde in good reaction performance, a method for producing the catalyst, and a method for producing an α,β-unsaturated carboxylic acid by using the catalyst. The present invention resides in a catalyst for producing an α,β-unsaturated carboxylic acid, wherein a metal is supported on a carrier with a total pore volume of 0.40 to 1.50 cc/g as measured by nitrogen gas adsorption method, or wherein palladium with an average particle diameter in the range of 1 to 8 nm is supported on the carrier.

6 Claims, No Drawings

CATALYST FOR PRODUCING α,β-UNSATURATED CARBOXYLIC ACID AND METHOD FOR PREPARATION THEREOF, AND METHOD FOR PRODUCING α,β-UNSATURATED CARBOXYLIC ACID

CROSS-REFERENCE TO RELATED APPLICATIONS

This application is a divisional of U.S. Ser. No. 10/588,973 filed Aug. 10, 2006, pending, which is a 371 application of PCT/JP05/01804 filed Feb. 8, 2005 and claims the benefit of JP 2004-033256 filed Feb. 10, 2004, JP2004-033276 filed Feb. 10, 2004, and JP2004-233287 filed Aug. 10, 2004.

TECHNICAL FIELD

The present invention relates to a catalyst for producing an α,β-unsaturated carboxylic acid through liquid-phase oxidation of an olefin or an α,β-unsaturated aldehyde, a method for producing the catalyst and a method for producing an α,β-unsaturated carboxylic acid by using the catalyst.

BACKGROUND ART

Many of α,β-unsaturated carboxylic acids are industrially useful. For example, acrylic acid or methacrylic acid is being used in a considerable amount for the application such as a raw material of synthetic resins. Although examples include gas-phase oxidation and liquid-phase oxidation of isobutene and a method by way of acetone cyanohydrin as a method for producing methacrylic acid, there is not a specifically advantageous method and methacrylic acid has been industrially produced by these several methods.

There has been many researches on a catalyst and a method for producing an α,β-unsaturated carboxylic acid through liquid-phase oxidation of an olefin or an α,β-unsaturated aldehyde with molecular oxygen. Examples include a method in the presence of gold supported catalyst (Patent Document 1), a method using a palladium metal catalyst (Patent Documents 2 to 6) and a method using a molybdenum compound and a palladium catalyst (Patent Document 7).

The catalysts disclosed in Patent Documents 2 to 7 contain palladium as a component of a catalyst, however, there is no description concerning particle diameter of palladium. Further, some of the catalysts disclosed in Patent Documents 1 to 7 are supported on a carrier such as activated carbon, alumina or silica. However, as for physical properties of these carriers, there is merely one description in Patent Document 1 as "it is preferable to use a hydrophobic carrier or a conventional carrier subjected to hydrophobic treatment", and there are no other descriptions, in those documents, referring to physical properties of these carriers.

Patent Document 1: Japanese Patent Application Laid-Open No. 2001-172,222.

Patent Document 2: Japanese Patent Application Laid-Open No. 60-155,148.

Patent Document 3: Japanese Patent Application Laid-Open No. 60-139,341.

Patent Document 4: Japanese Patent Application Laid-Open No. 60-139,643.

Patent Document 5: U.S. Pat. No. 4,435,598.

Patent Document 6: International Publication No. WO 02/083,299.

Patent Document 7: Japanese Patent Application Laid-Open No. 56-59,722.

DISCLOSURE OF INVENTION

Problem to be Solved by the Invention

When the present inventors produced acrylic acid from propylene by using the catalyst produced according to the methods of Examples described in Patent Documents 1 to 7, it was found that by-products such as various polymers and oligomers were produced in large amount in addition to the by-products described in Patent Documents 1 to 7 (for example, acetaldehyde, acetone, acrolein, acetic acid and carbon dioxide). In Patent Documents 1 to 7, these polymers and oligomers were not captured, and hence, the actual selectivity to acrylic acid and the yield of acrylic acid in view of these by-products were found to be lower than those described in Examples of Patent Documents 1 to 7. Consequently, the reaction performance obtained in the method for producing an α,β-unsaturated carboxylic acid in Patent Documents 1 to 7 was not sufficient yet, and hence, further improvement on this point has been desired.

The object of the present invention is to provide a catalyst which can produce an α,β-unsaturated carboxylic acid through liquid-phase oxidation of an olefin or an α,β-unsaturated aldehyde in good reaction performance, a method for producing the catalyst and a method for producing an α,β-unsaturated carboxylic acid by using the catalyst.

Means for Solving Problem

The present inventors have found that the catalyst performance is considerably influenced by physical properties of a carrier to be used in producing a catalyst, in particular, by pore volume, and thus have completed the present invention. The present inventors have also found that, when palladium is used as a component of a catalyst, the catalyst performance is considerably influenced by a particle diameter of palladium in the catalyst produced, and thus have completed the present invention.

A catalyst for producing an α,β-unsaturated carboxylic acid of the present invention is a catalyst for producing an α,β-unsaturated carboxylic acid through liquid-phase oxidation of an olefin or an α,β-unsaturated aldehyde and is the following:

(i) A catalyst for producing an α,β-unsaturated carboxylic acid, wherein a metal is supported on a carrier with a total pore volume of 0.40 to 1.50 cc/g as measured by nitrogen gas adsorption method; or (ii) A catalyst for producing an α,β-unsaturated carboxylic acid, wherein palladium with an average particle diameter in the range of 1 to 8 nm is supported on a carrier.

A method for producing the catalyst for producing an α,β-unsaturated carboxylic acid of the present invention is a method for producing the catalyst for producing an α,β-unsaturated carboxylic acid of the above (i), wherein a metal compound is reduced by a reducing agent in the presence of the above carrier.

A method for producing the catalyst for producing an α,β-unsaturated carboxylic acid of the present invention is a method for producing the catalyst for producing an α,β-unsaturated carboxylic acid of the above (ii), wherein a palladium compound is reduced by a reducing agent in the presence of the above carrier.

A method for producing an α,β-unsaturated carboxylic acid of the present invention is a method for producing an α,β-unsaturated carboxylic acid through liquid-phase oxidation of an olefin or an α,β-unsaturated aldehyde with molecular oxygen in the presence of the catalyst for producing an α,β-unsaturated carboxylic acid of the above (i) or (ii).

Effect of the Invention

According to the present invention, a catalyst which can produce an α,β-unsaturated carboxylic acid through liquid-phase oxidation of an olefin or an α,β-unsaturated aldehyde in good reaction performance, a method for producing the catalyst and a method for producing an α,β-unsaturated carboxylic acid by using the catalyst can be provided.

BEST MODE FOR CARRYING OUT THE INVENTION (1) Catalyst for Producing an α,β-Unsaturated Carboxylic Acid The catalyst for producing an α,β-unsaturated carboxylic acid of the present invention (hereinafter, sometimes expressed as "catalyst") is a catalyst for producing an α,β-unsaturated carboxylic acid through liquid-phase oxidation of an olefin or an α,β-unsaturated aldehyde and is the following:

(i) A catalyst for producing an α,β-unsaturated carboxylic acid, wherein a metal is supported on a carrier with a total pore volume of 0.40 to 1.50 cc/g as measured by nitrogen gas adsorption method; or (ii) A catalyst for producing an α,β-unsaturated carboxylic acid, wherein palladium with an average particle diameter in the range of 1 to 8 nm is supported on a carrier.

By using the above-mentioned catalyst, an α,β-unsaturated carboxylic acid can be produced through liquid-phase oxidation of an olefin or an α,β-unsaturated aldehyde in good reaction performance. The catalyst of the present invention is especially effective for liquid-phase oxidation of propylene and isobutylene among olefins and liquid-phase oxidation of acrolein and methacrolein among α,β-unsaturated aldehydes.

The catalyst of the present invention is a supported catalyst in which a metal is supported on a carrier. Hereinafter, a carrier and a metal, which can be used as the catalyst of the present invention, will be explained.

(1-1) Carrier

The kind of the carrier of the present invention is not particularly limited and typical carriers such as activated carbon, carbon black, silica, alumina, magnesia, calcia, zirconia and titania can be used. Among them, activated carbon or silica is preferably used. Activated carbon is generally produced through the processes of carbonization, granulation, activation, washing, drying and pulverization, and these producing processes are not particularly limited in the present invention. A carbonaceous material which is the raw material of activated carbon is not particularly limited either, and various raw materials such as coconut shell, coal, lignin and synthetic resin can be used. The process of activation is not particularly limited either, and water vapor, carbon dioxide, oxygen, phosphoric acid, phosphate and zinc chloride can be used for activation. The activated carbon after the activation process is washed with mineral acid, hydrochloric acid and water, if necessary, and dried to be put to use. Among impurities contained in the product activated carbon, it is preferable to keep the amount of chlorine as small as possible because chlorine sometimes causes bad effects on the catalyst performance. Therefore, an activated carbon produced by using zinc chloride or hydrochloric acid is preferably washed sufficiently to remove the contained chlorine. The shape of the activated carbon is not particularly limited either and the activated carbon having various shapes such as powder, sphere, pellet and fiber can be used. The BET specific surface area of the activated carbon is preferably 300 m$^2$/g or more, particularly preferably 600 m$^2$/g or more, and preferably 4,000 m$^2$/g or less, particularly preferably 2,500 m$^2$/g or less.

One embodiment of the catalyst of the present invention is to select and use a carrier with a total pore volume of 0.40 to 1.50 cc/g as measured by nitrogen gas adsorption method. By using such a carrier, an α,β-unsaturated carboxylic acid can be produced through liquid-phase oxidation of an olefin or an α,β-unsaturated aldehyde in high selectivity and high productivity. Hereinafter, the constitution of the above carrier and the method for producing the carrier will be explained.

In particular, to obtain a target product in high selectivity, it is preferable to select a carrier with a total pore volume of 0.40 to 0.80 cc/g. The total pore volume is more preferably 0.47 cc/g or more, further preferably 0.70 cc/g or less, and furthermore preferably 0.67 cc/g or less. By using a carrier which fulfills such requirements, a target product such as acrylic acid or methacrylic acid can be obtained in good selectivity with little formation of by-products. The selectivity of the target product is improved because selecting a smaller range within the aforementioned range of the total pore volume is supposed to suppress the formation of by-products such as oligomers. Further, in this case, a proportion of the pore volume of the mesopore having a pore size of from 2 nm through 50 nm to the total pore volume is preferably 40% or less to the total pore volume, more preferably 35% or less, furthermore preferably 30% or less and particularly preferably 20% or less. Further, the above proportion of the pore volume of the mesopore is preferably 5% or more to the total pore volume, more preferably 7% or more and furthermore preferably 9% or more. In this case, in particular, when the total pore volume are the same, the carrier with lower proportion of the mesopore is supposed to have the tendency to form lesser amount of by-products such as oligomers, and hence, improves the selectivity. Further, the BET specific surface area of the carrier is preferably 600 m$^2$/g or more, more preferably 800 m$^2$/g or more, and preferably 2,000 m$^2$/g or less, more preferably 1,500 m$^2$/g or less.

In particular, to obtain a target product in high productivity, it is preferable to select the carrier with a total pore volume of 0.70 to 1.50 cc/g. The total pore volume is more preferably 0.80 cc/g or more, furthermore preferably 0.90 cc/g or more, and more preferably 1.40 cc/g or less, furthermore preferably 1.30 cc/g or less. By using a carrier which fulfills such requirements, a target product such as acrylic acid or methacrylic acid can be obtained in good productivity with high activity of the catalyst. The productivity of the target product is improved because selecting a larger range within the aforementioned range of the total pore volume is supposed to make internal pore diffusion of reactants and products easy. Further, a proportion of the pore volume of the mesopore having a pore size of from 2 nm through 50 nm to the total pore volume is preferably 10% or more to the total pore volume, more preferably 20% or more, furthermore preferably 30% or more and particularly preferably 40% or more. Further, the above proportion is preferably 65% or less, more preferably 60% or less and furthermore preferably 55% or less. In this case, in particular, when the total pore volumes are the same, the carrier with larger proportion of the mesopore is supposed to have the tendency to make internal pore diffusion easier, and hence, improves the production efficiency. Further, the BET specific surface area of the carrier is preferably 100 m²/g or more, more preferably 300 m²/g or more, and preferably 5,000 m²/g or less, more preferably 4,000 m²/g or less.

The total pore volume, the pore volume of the mesopore having a pore size of from 2 nm through 50 nm and the BET specific surface area of the carrier are measured by, for example, Surface Area and Porosimetry Analyzer, TriStar 3000 (trade name), manufactured by Micromeritics Instrument Corporation.

(1-2) Metal

The metal to be supported on the carrier is not particularly limited as long as it functions as a catalyst of liquid-phase oxidation, however, noble metal is preferable, palladium or gold is more preferable and palladium is particularly preferable. The metal can be used alone or in combination of two or more kinds. Further, the metal may contain another metal which does not function as a catalyst of liquid-phase oxidation. The content of the metal which does not function as a catalyst of liquid-phase oxidation is preferably 50 atomic % or less from the viewpoint of catalyst activity.

One embodiment of the catalyst of the present invention is a catalyst in which palladium with an average particle diameter in the range of 1 to 8 nm is supported on a carrier. By selecting palladium as a metal and controlling its average particle diameter to fall in the range of 1 to 8 nm, a catalyst which can produce an α,β-unsaturated carboxylic acid from an α,β-unsaturated aldehyde in high yield can be obtained. The above-mentioned average particle diameter is preferably 1.2 nm or more, more preferably 1.4 nm or more and preferably 7 nm or less, more preferably 6 nm or less. When the average particle diameter of palladium is outside the above range, the activity of the catalyst containing the above palladium is liable to be lowered, and hence, the yield of an α,β-unsaturated carboxylic acid is liable to be lowered. At this time, the catalyst may contain a metal other than palladium, however, the content of the metal other than palladium is preferably 50 atomic % or less from the viewpoint of catalyst activity.

The average particle diameter of palladium mentioned above means a value measured with palladium in the catalyst by transmission electron microscope, which is concretely calculated as follows.

Print out an image of transmission electron microscope with the same magnification as that of the observation, and randomly sample 50 points of the palladium regions in the field of view and measure particle diameter of each palladium region; measure the particle diameter by assuming its shape to be circular because the shape of the palladium region is almost circular; and carry out these operations with 3 fields of view and average the measured values to obtain an average particle diameter.

Here, the observation by transmission electron microscope is carried out with a magnification under which the measurement of a palladium particle diameter is possible.

The average particle diameter of palladium in the catalyst varies depending on various conditions such as a kind of carrier and BET specific surface area of a carrier to be used, a kind of solvent and mixing ratio in the case of mixed solvent to be used in the preparation of the catalyst, a kind and concentration of a palladium compound which is a raw material of the catalyst, and temperature and time of reducing the palladium compound. In the present invention, it is necessary to control the average particle diameter of palladium in the catalyst to be obtained to fall in the above-mentioned range by properly selecting and setting these conditions.

(2) A Method for Producing a Catalyst for Producing an α,β-Unsaturated Carboxylic Acid In the next place, a method for producing the above-mentioned catalyst for producing an α,β-unsaturated carboxylic acid of the present invention will be explained.

The method for producing the catalyst of the present invention is not particularly limited, however, it is preferable to select a method in which a metal compound is reduced by a reducing agent in the presence of a carrier. Concretely, the catalyst can be prepared, for example, by a liquid-phase reduction method in which a metal compound solution with dispersed carrier is prepared and a reducing agent is added to it to reduce the metal compound or by a gas-phase reduction method in which a carrier impregnated with a metal compound solution is dried and then subjected to reduction in a reducing atmosphere. Among them, the liquid-phase reduction method is preferable. Hereinafter, a method for producing the catalyst by the liquid-phase reduction method will be explained.

As the metal compound to be used, it is preferably chlorides, oxides, acetates, nitrates, sulfates, tetraammine complex or acetylacetonato complex of the metal which becomes the catalyst, more preferably chlorides, oxides, acetates, nitrates or sulfates of the metal, furthermore preferably chlorides, acetates or nitrates of the metal. These compounds can be used alone or in combination of two or more kinds.

Further, as these metal compounds, it is also preferable to use those which do not substantially contain chlorine as an impurity. More concretely, it is preferable that chlorine content in the metal compound is 1,000 ppm or less. In other words, it is preferable to use metal compounds which do not contain chlorine such as acetates, nitrates or bisacetylacetonato complexes. When palladium is selected as the metal, for example, palladium acetate, palladium nitrate or bisacetylacetonatopalladium can be suitably used.

As the solvent to dissolve the metal compound, it is properly selected in view of solubility of the metal compound and the reducing agent and dispersibility of the carrier. Water, alcohols, ketones, organic acids, hydrocarbons or mixed solvent of two or more kinds selected from these groups can be used. As the solvent, at least one organic solvent selected from the group consisting of alcohols, ketones and organic acids is preferable, and at least one organic solvent selected from the group consisting of organic acids having carbon number of 2 to 6, tertiary butanol and ketones having carbon number of 3 to 6 is more preferable.

It is also preferable to use a mixed solvent of water and an organic solvent because a catalyst with better performance can be prepared. When the mixed solvent of water and an organic solvent is used, a mixed solvent of water and at least one organic solvent selected from the group consisting of alcohols, ketones and organic acids is preferable. Among them, a mixed solvent of water and at least one organic solvent selected from organic acids is more preferable. As the organic acids, at least one organic acid selected from the group consisting of acetic acid, propionic acid, n-butyric acid, iso-butyric acid, n-valeric acid and iso-valeric acid is preferable. Among them, n-valeric acid or acetic acid is particularly preferable. In this case, the amount of water is not particularly limited, however, it is preferably 5% by weight or more to the weight of the mixed solvent, more preferably 8% by weight or more. In addition, the amount of water mentioned above is preferably 60% by weight or less, more preferably 50% by weight or less, furthermore preferably 40% by weight or less. In the case of mixed solvent, it is preferable that the solvent is homogeneous, while it may be heterogeneous.

A carrier and a metal compound are added to the above-mentioned solvent in a desired order or simultaneously to prepare a metal compound solution with dispersed carrier. Concentration of the metal compound is preferably 0.1% by weight or more, more preferably 0.2% by weight or more, particularly preferably 0.5% by weight or more. Besides, concentration of the above metal compound is preferably 20% by weight or less, more preferably 10% by weight or less, furthermore preferably 7% by weight or less and particularly preferably 4% by weight or less.

In the next place, a reducing agent is added to the metal compound solution with dispersed carrier to reduce the metal compound, to obtain a catalyst in which the metal is supported on the carrier.

The reducing agent to be used is not particularly limited and any material can be used as long as it has the ability to reduce a metal in its oxidized state in the metal compound. For example, hydrazine, formaldehyde, sodium borohydride, hydrogen, formic acid, formates, alcohols and olefins can be used. Among them, at least one compound selected from the group consisting of formaldehyde, propylene, isobutylene, 1-butene and 2-butene is preferable and formaldehyde, propylene or isobutylene is more preferable.

When a gas such as propylene is used as the reducing agent, it is preferable to charge a metal compound solution with dispersed carrier in a pressure device such as autoclave and to pressurize the inside with the reducing agent to carry out reduction. The pressure is preferably 0.1 to 1.0 MPa (gauge pressure; hereinafter, pressure is all expressed in gauge pressure).

When the reducing agent is liquid or solid, reduction can be carried out by adding the reducing agent in a metal compound solution with dispersed carrier. In this case, the amount of the reducing agent is preferably 1 to 50 mols to 1 mol of the metal compound.

Temperature of the system at the time of reduction and reducing time are different depending on a method of reduction, a carrier and a metal compound to be used, solvent, a reducing agent and the like and cannot be absolutely said. In the case of liquid-phase reduction method, reducing temperature is preferably −5° C. or higher, more preferably 0° C. or higher, furthermore preferably 15° C. or higher, and preferably 150° C. or lower, more preferably 100° C. or lower, furthermore preferably 80° C. or lower. Reducing time is preferably 0.1 hour or more, more preferably 0.25 hour or more, furthermore preferably 0.5 hour or more, and is preferably 24 hours or less, more preferably 4 hours or less, furthermore preferably 3 hours or less and particularly preferably 2 hours or less.

After reduction, a catalyst in which the metal is supported on the carrier is separated from the dispersion. The method of separation is not particularly limited and, for example, filtration or centrifugation can be used. The catalyst thus separated is properly dried. The drying method is not particularly limited and various methods can be used.

Concentration of the metal contained in the residual solution separated from the catalyst after reduction is preferably 10 mg/l or less. This amount can be adjusted by concentration of the metal compound before reduction, a reducing condition or the like. The presence of the metal in the solution can be easily confirmed by adding a reducing agent such as hydrazine, and the amount of the metal in the solution can be determined quantitatively with an elemental analysis such as ICP.

The supported metal ratio of the catalyst is preferably 0.1% by weight or more to the carrier before the metal is supported, more preferably 0.5% by weight or more, furthermore preferably 1% by weight or more and particularly preferably 4% by weight or more. Besides, the supported metal ratio of the catalyst is preferably 40% by weight or less to the weight of the carrier before the metal is supported, more preferably 30% by weight or less, furthermore preferably 20% by weight or less and particularly preferably 15% by weight or less. The supported ratio can be obtained from weight of the carrier used in the preparation of the catalyst, weight of the metal in the metal compound and weight of the metal contained in the residual solution separated from the catalyst after reduction.

The catalyst thus produced may be used for the reaction in the state of dispersion after washing with a solvent or in the state of isolated form by centrifugation or filtration.

The catalyst may be activated previous to being served to liquid-phase oxidation. The method for activation is not particularly limited and various methods can be used. As the method for activation, a method of heating under reducing atmosphere in a flow of hydrogen is preferable.

(3) A Method for Producing an α,β-Unsaturated Carboxylic Acid

In the next place, a method for producing an α,β-unsaturated carboxylic acid through liquid-phase oxidation of an olefin or an α,β-unsaturated aldehyde by using the catalyst for producing an α,β-unsaturated carboxylic acid of the present invention thus obtained will be explained.

Examples of the raw olefin of the liquid-phase oxidation include propylene, isobutylene and 2-butene. Examples of the raw α,β-unsaturated aldehyde include acrolein, methacrolein, crotonaldehyde (β-methylacrolein) and cinnamaldehyde (β-phenylacrolein). The raw olefin or the raw α,β-unsaturated aldehyde may contain a small amount of impurities such as a saturated hydrocarbon and/or a saturated lower aldehyde.

In the case that an olefin is used as the raw material, the α,β-unsaturated carboxylic acid to be produced in the liquid-phase oxidation has the same carbon skeleton as the original olefin. Further, in the case that an α,β-unsaturated aldehyde is used as the raw material, its aldehyde group changes into carboxyl group in the α,β-unsaturated carboxylic acid to be produced.

The catalyst of the present invention is suitable for producing acrylic acid from propylene or acrolein, or methacrylic acid from isobutylene or methacrolein through liquid-phase oxidation.

As a source of molecular oxygen to be used in the reaction, air is economical, and also pure oxygen or mixed gas of air and pure oxygen can be used. If necessary, mixed gas in which air or pure oxygen is diluted with nitrogen, carbon dioxide, water vapor or the like can be used too.

A solvent to be used in the liquid-phase oxidation reaction is not particularly limited and, for example, water; alcohols such as tertiary butanol and cyclohexanol; ketones such as acetone, methyl ethyl ketone and methyl isobutyl ketone; organic acids such as acetic acid, propionic acid, n-butyric acid, iso-butyric acid, n-valeric acid, iso-valeric acid; organic acid esters such as ethyl acetate and methyl propionate; hydrocarbons such as hexane, cyclohexane and toluene; or a mixed solvent consisting of two or more kinds of solvents selected from these groups can be used. Among them, at least one solvent selected from the group consisting of alcohols, ketones, organic acids and organic acid esters is preferable, and at least one solvent selected from the group consisting of organic acids having carbon number of 2 to 6, tertiary butanol and ketones having carbon number of 3 to 6 is more preferable, and a solvent containing any one of tertiary butanol, acetic acid and n-valeric acid is particularly preferable. Further, a mixed solvent of water and at least one solvent selected from the group consisting of alcohols, ketones, organic acids and organic acid esters is preferable because the performance of the liquid-phase oxidation is further improved by using this solvent. In this case, the amount of water is not particularly limited, however, it is preferably 2% by weight or more to the weight of the mixed solvent, more preferably 5% by weight or more, and preferably 70% by weight or less to the weight of the mixed solvent, more preferably 50% by weight or less. It is desirable that the solvent is homogeneous, while it can be used in a heterogeneous state.

Although the liquid-phase oxidation reaction may be carried out either in a continuous system or in a batch system, a continuous system is preferable for industry in view of productivity.

The amount to be used of the raw olefin or the raw $\alpha,\beta$-unsaturated aldehyde is generally 0.1 part by weight or more to 100 parts by weight of the solvent, and preferably 0.5 part by weight or more; and generally 20 parts by weight or less, and preferably 10 parts by weight or less.

The amount to be used of the molecular oxygen is preferably 0.1 mol or more to 1 mol of the raw olefin or the raw $\alpha,\beta$-unsaturated aldehyde, more preferably 0.3 mol or more and particularly preferably 0.5 mol or more. The above amount to be used is preferably 30 mols or less, more preferably 25 mols or less, furthermore preferably 20 mols or less, particularly preferably 15 mols or less and most preferably 10 mols or less.

The catalyst is generally used in a dispersed state in a reaction liquid in which liquid-phase oxidation is carried out, while it may be used in a fixed bed. The amount of the catalyst to be used is preferably 0.1 part by weight or more as the catalyst existing in the reactor to 100 parts by weight of solution existing in the reactor, more preferably 0.5 part by weight or more, and particularly preferably 1 part by weight or more. The above amount to be used is preferably 30 parts by weight or less, more preferably 20 parts by weight or less, and particularly preferably 15 parts by weight or less.

The reaction temperature and the reaction pressure are properly set depending on the solvent and the raw materials to be used. The reaction temperature is preferably 30° C. or more, more preferably 50° C. or more, furthermore preferably 60° C. or more and particularly preferably 70° C. or more. The reaction temperature is preferably 200° C. or less, more preferably 150° C. or less. The reaction pressure is preferably atmospheric pressure (0 MPa) or more, more preferably 0.5 MPa or more and furthermore preferably 2 MPa or more, and preferably 10 MPa or less, more preferably 7 MPa or less and furthermore preferably 5 MPa or less.

When the reaction is carried out under pressure, it is preferable to use an autoclave having a stirring function.

EXAMPLES

Hereinafter, the present invention is further explained concretely with reference to examples and comparative examples, however, the present invention is not limited to those examples. In the following examples and comparative examples, "part" means part by mass.

(Analysis of a Raw Material and a Product)

Analysis of a raw material and a product was carried out by using gas chromatography. The conversion of an olefin or an $\alpha,\beta$-unsaturated aldehyde; the selectivity to an $\alpha,\beta$-unsaturated aldehyde to be produced; the selectivity to a polymer/oligomer to be produced; the selectivity to an $\alpha,\beta$-unsaturated carboxylic acid to be produced, and the yield and productivity of an $\alpha,\beta$-unsaturated carboxylic acid to be produced are defined as follows:

The conversion (%) of an olefin or an $\alpha,\beta$-unsaturated aldehyde=$(B/A)\times 100$;

The selectivity (%) to an $\alpha,\beta$-unsaturated aldehyde= $(C/B)\times 100$;

The selectivity (%) to an $\alpha,\beta$-unsaturated carboxylic acid=$(D/B)\times 100$;

The selectivity (%) to a polymer/oligomer=$(E/B)\times 100$;

The yield (%) of an $\alpha,\beta$-unsaturated carboxylic acid= $(D/A)\times 100$; and The productivity (g/(g·h)) of an $\alpha,\beta$-unsaturated carboxylic acid=$F/(G\times H)$ In the above formulae, A represents mol number of an olefin or an $\alpha,\beta$-unsaturated aldehyde supplied; B represents mol number of an olefin or an $\alpha,\beta$-unsaturated aldehyde reacted; C represents mol number of an $\alpha,\beta$-unsaturated aldehyde produced; D represents mol number of an $\alpha,\beta$-unsaturated carboxylic acid produced; E represents reduced mol number of a polymer and oligomer produced based on an olefin or an $\alpha,\beta$-unsaturated aldehyde, which is calculated by dividing total weight (unit: g) of a polymer and oligomer produced by molecular weight of an olefin or an $\alpha,\beta$-unsaturated aldehyde supplied; F represents weight (unit: g) of an $\alpha,\beta$-unsaturated carboxylic acid produced; G represents weight (unit: g) of a metal contained in a catalyst used; and H represents reaction time (unit: hour). Further, in the case of liquid-phase oxidation reaction of an $\alpha,\beta$-unsaturated aldehyde, C/B is 0.

(Measurements of Physical Properties of a Carrier)

Measurements of pore volume and pore size distribution of a carrier were carried out with fixed volume method based on nitrogen gas adsorption method by using Surface Area and Porosimetry Analyzer, TriStar 3000 (trade name), manufactured by Micromeritics Instrument Corporation. The pore size measurable by this method is in the range of about from 1 to 100 nm, and all the pore volumes and pore size distributions described in the present invention were calculated based on changes in the quantity of nitrogen adsorbed (adsorption isotherm) according to the direction of raising the relative pressure (adsorption equilibrated pressure/saturated vapor pressure).

In the above measurement, total pore volume per unit weight of a carrier and BET specific surface area were measured by using t-plot method. Further, pore volume of pores having a pore size of from 2 nm through 50 nm (mesopore) was calculated by using BJH method, and a proportion of the mesopore to the total pore volume was calculated.

(Average Particle Diameter of Palladium in a Palladium-Containing Supported Catalyst)

Average particle diameter of palladium in a palladium-containing supported catalyst was measured with transmission electron microscope, and concretely, calculated as follows. Print out an image of transmission electron microscope with the same magnification as that of the observation, and randomly sample 50 points of the palladium regions in the field of view and measure particle diameter of each palladium region; measure the particle diameter by assuming its shape to be circular because the shape of the palladium region is almost circular; and carry out these operations with 3 fields of view and average the measured values to obtain an average particle diameter.

Example 1

Preparation of Catalyst

To 55 parts of 88% by weight n-valeric acid aqueous solution, 1 part of palladium acetate (manufactured by N.E.CHEMCAT Corporation) was dissolved. The resultant solution was introduced into an autoclave to which 5 parts of activated carbon made from synthesized raw material (total pore volume: 0.64 cc/g; BET specific surface area: 1,313 $m^2/g$; proportion of the pore volume of mesopore having a pore size of from 2 nm through 50 nm to the total pore volume: 7.8%) manufactured by KURARAY CHEMICAL Co., Ltd. was added. The resultant mixture was stirred. After propylene was introduced to the system pressure of 0.5 MPa, the resultant system was heated to 50° C. in 30 minutes and reduced for 30 minutes. After the reduction, palladium supported catalyst thus obtained was filtered, washed and replaced by 88% by weight acetic acid aqueous solution, and filtered. Finally, palladium-containing supported catalyst, the supported ratio of which was 10% by weight was obtained.

(Evaluation of Reaction)

To the autoclave, 135 parts of 88% by weight acetic acid aqueous solution containing 200 ppm of para-metoxyphenol (polymerization inhibitor) was introduced, and 5.5 parts of the above-mentioned palladium-containing supported catalyst, the supported ratio of which was 10% by weight was added. Further, 4.5 parts of methacrolein was added to it and the reactor was shut tight. Then, the temperature was raised to 90° C. while stirring. Air was introduced to the system pressure of 3.2 MPa and oxidation reaction of methacrolein was carried out for 20 minutes. The amount of molecular oxygen used in the oxidation reaction was 0.76 mol to 1 mol of methacrolein. After the reaction was finished, the autoclave was cooled to around the room temperature and the reaction liquid was taken out. The reaction liquid from which the catalyst had been separated was analyzed with gas chromatography.

As the result, the conversion of methacrolein was 84.0%, the selectivity to methacrylic acid was 83.2% and the productivity of methacrylic acid was 23.1 g/(g·h).

Example 2

The preparation of the catalyst and the evaluation of the reaction were carried out in the same manner as in Example 1 except that coconut shell activated carbon (total pore volume: 0.49 cc/g; BET specific surface area: 988 $m^2/g$; proportion of the pore volume of mesopore having a pore size of from 2 nm through 50 nm to the total pore volume: 10%) manufactured by KURARAY CHEMICAL Co., Ltd. was used as a carrier.

As the result, the conversion of methacrolein was 89.7%, the selectivity to methacrylic acid was 84.7% and the productivity of methacrylic acid was 25.2 g/(g·h).

Example 3

The preparation of the catalyst and the evaluation of the reaction were carried out in the same manner as in Example 1 except that coal-derived activated carbon (total pore volume: 0.46 cc/g; BET specific surface area: 753 $m^2/g$; proportion of the pore volume of mesopore having a pore size of from 2 nm through 50 nm to the total pore volume: 33%) manufactured by DAINEN CO., LTD. was used as a carrier.

As the result, the conversion of methacrolein was 84.4%, the selectivity to methacrylic acid was 80.1% and the productivity of methacrylic acid was 22.4 g/(g·h).

Example 4

The preparation of the catalyst and the evaluation of the reaction were carried out in the same manner as in Example 1 except that activated carbon made from synthesized raw material (total pore volume: 0.75 cc/g; BET specific surface area: 1,613 $m^2/g$; proportion of the pore volume of mesopore having a pore size of from 2 nm through 50 nm to the total pore volume: 4.0%) manufactured by KURARAY CHEMICAL Co., Ltd. was used as a carrier.

As the result, the conversion of methacrolein was 78.3%, the selectivity to methacrylic acid was 80.1% and the productivity of methacrylic acid was 20.8 g/(g·h).

Example 5

The preparation of the catalyst and the evaluation of the reaction were carried out in the same manner as in Example 1 except that coal-derived activated carbon (total pore volume: 0.92 cc/g; BET specific surface area: 1,345 $m^2/g$; proportion of the pore volume of mesopore having a pore size of from 2 nm through 50 nm to the total pore volume: 52%) manufactured by DAINEN CO., LTD. was used as a carrier and reaction time was 11 minutes.

As the result, the conversion of methacrolein was 90.3%, the selectivity to methacrylic acid was 77.3% and the productivity of methacrylic acid was 42.1 g/(g·h).

Example 6

The preparation of the catalyst and the evaluation of the reaction were carried out in the same manner as in Example 1 except that activated carbon made from synthesized raw material (total pore volume: 1.27 cc/g; BET specific surface area: 2,587 $m^2/g$; proportion of the pore volume of mesopore having a pore size of from 2 nm through 50 nm to the total pore volume: 26%) manufactured by KURARAY CHEMICAL Co., Ltd. was used as a carrier and reaction time was 11 minutes.

As the result, the conversion of methacrolein was 89.5%, the selectivity to methacrylic acid was 78.3% and the productivity of methacrylic acid was 42.3 g/(g·h).

Example 7

The preparation of the catalyst and the evaluation of the reaction were carried out in the same manner as in Example 1 except that charcoal-derived activated carbon (total pore volume: 1.30 cc/g; BET specific surface area: 1,692 $m^2/g$; proportion of the pore volume of mesopore having a pore size of from 2 nm through 50 nm to the total pore volume: 58%) manufactured by Norit Corporate was used as a carrier and reaction time was 15 minutes.

As the result, the conversion of methacrolein was 86.9%, the selectivity to methacrylic acid was 76.2% and the productivity of methacrylic acid was 29.3 g/(g·h).

Comparative Example 1

The preparation of the catalyst and the evaluation of the reaction were carried out in the same manner as in Example 1 except that coal-derived activated carbon (total pore volume: 1.61 cc/g; BET specific surface area: 3,174 m²/g; proportion of the pore volume of mesopore having a pore size of from 2 nm through 50 nm to the total pore volume: 35%) manufactured by THE KANSAI COKE AND CHEMICALS CO., LTD. was used as a carrier.

As the result, the conversion of methacrolein was 35.0%, the selectivity to methacrylic acid was 24.3% and the productivity of methacrylic acid was 2.8 g/(g·h).

Comparative Example 2

The preparation of the catalyst and the evaluation of the reaction were carried out in the same manner as in Example 1 except that wood-derived activated carbon (total pore volume: 1.61 cc/g; BET specific surface area: 1,680 m²/g; proportion of the pore volume of mesopore having a pore size of from 2 nm through 50 nm to the total pore volume: 68%) manufactured by Norit Corporate was used as a carrier.

As the result, the conversion of methacrolein was 83.1%, the selectivity to methacrylic acid was 54.5% and the productivity of methacrylic acid was 15.0 g/(g·h).

Comparative Example 3

The preparation of the catalyst and the evaluation of the reaction were carried out in the same manner as in Example 1 except that activated carbon made from synthesized raw material (total pore volume: 0.37 cc/g; BET specific surface area: 690 m²/g; proportion of the pore volume of mesopore having a pore size of from 2 nm through 50 nm to the total pore volume: 2.7%) manufactured by KURARAY CHEMICAL Co., Ltd. was used as a carrier.

As the result, the conversion of methacrolein was 50.5%, the selectivity to methacrylic acid was 65.2% and the productivity of methacrylic acid was 10.9 g/(g·h).

A summary of the physical properties of the carriers used and the results of the reaction in Examples 1 to 7 and Comparative Examples 1 to 3 are shown in Table 1. In Examples 1 to 7 where a carrier with a total pore volume of 0.40 to 1.50 cc/g was used, it was found that the selectivity to methacrylic acid and the productivity of methacrylic acid were good.

Further, in Examples 1 to 4 where a carrier with a smaller total pore volume was used, it was found that the selectivity to methacrylic acid was particularly good. Moreover, in Examples 5 to 7 where a carrier with a larger total pore volume was used, it was found that the productivity of methacrylic acid was particularly good.

TABLE 1

| | Physical properties of carrier | | Reaction time (min) | Selectivity to methacrolein (%) | Selectivity to methacrylic acid (%) | Productivity of methacrylic acid (g/(g·h)) |
|---|---|---|---|---|---|---|
| | Total pore volume (cc/g) | Proportion of pore size of 2 to 50 nm (%) | | | | |
| Ex. 1 | 0.64 | 7.8 | 20 | 84.0 | 83.2 | 23.1 |
| Ex. 2 | 0.49 | 10 | 20 | 89.7 | 84.7 | 25.2 |
| Ex. 3 | 0.46 | 33 | 20 | 84.4 | 80.1 | 22.4 |
| Ex. 4 | 0.75 | 4.0 | 20 | 78.3 | 80.1 | 20.8 |
| Ex. 5 | 0.92 | 52 | 11 | 90.3 | 77.3 | 42.1 |
| Ex. 6 | 1.27 | 26 | 11 | 89.5 | 78.3 | 42.3 |
| Ex. 7 | 1.30 | 58 | 15 | 86.9 | 76.2 | 29.3 |
| Comp. Ex. 1 | 1.61 | 35 | 20 | 35.0 | 24.3 | 2.8 |
| Comp. Ex. 2 | 1.61 | 68 | 20 | 83.1 | 54.5 | 15.0 |
| Comp. Ex. 3 | 0.37 | 2.7 | 20 | 50.5 | 65.2 | 10.9 |

Example 8

Preparation of Catalyst

To 20 parts of acetic acid, 1.05 parts of palladium acetate (manufactured by N.E.CHEMCAT Corporation) was dissolved. The resultant solution was added to 10 parts of silica carrier (total pore volume: 0.68 cc/g; BET specific surface area: 450 m²/g; proportion of the pore volume of mesopore having a pore size of from 2 nm through 50 nm to the total pore volume: 100%) and shaken. The resultant mixture was evaporated. Then it was calcined at 450° C. in the air for 3 hours. To the catalyst precursor thus obtained, 13 parts of 37% by weight formaldehyde aqueous solution was added. The resultant mixture was heated to 70° C., and kept for 2 hours while stirring, filtered under reduced pressure, and the filter cake was washed and filtered by water and 75% by weight t-butanol aqueous solution. Finally, palladium-containing supported catalyst, the supported ratio of which was 5% by weight, was obtained.

(Evaluation of Reaction)

To an autoclave, the whole catalyst (10.5 parts) obtained in the above-mentioned method, 100 parts of 75% by weight t-butanol aqueous solution as a reaction solvent and 0.02 part of p-metoxyphenol were introduced, and the autoclave was shut tight. Then, 2.75 parts of isobutylene was introduced to it and stirring of the system was carried out (number of revolutions: 1,000 rpm) and the temperature of the system was raised to 90° C. When the temperature reached 90° C., nitrogen was introduced into the autoclave to the internal pressure of 2.3 MPa, and the compressed air was introduced into the autoclave to the internal pressure of 4.6 MPa. Every time when the internal pressure dropped by 0.1 MPa with the progress of the reaction, oxygen gas was introduced to compensate this internal pressure of 0.1 MPa, and this operation was repeated 10 times. After the 10th introduction of oxygen, when the internal pressure dropped by 0.1 MPa, the reaction was finished. At this time, the reaction time was 56 minutes. In the oxidation reaction, 3.48 mols of molecular oxygen to 1 mol of isobutylene was used.

After the reaction was finished, inside of the autoclave was cooled in ice bath. A gas sampling bag was attached to a gas outlet port of the autoclave and the product gas was recovered by opening the gas outlet port and reducing the internal pressure of the reactor. The reaction liquid containing the catalyst was taken out from the autoclave, and the catalyst was separated by using membrane filter to recover the reaction solution. The recovered reaction solution and the collected gas were analyzed with gas chromatography and the conversion and the selectivity were calculated.

As the result, the conversion of isobutylene was 90.7%, the selectivity to methacrolein was 28.2%, the selectivity to methacrylic acid was 28.6% and the productivity of methacrylic acid was 2.2 g/(g·h).

Example 9

The same method as in Example 8 was carried out except that a carrier to be used was changed to Y-type zeolite (total pore volume: 0.50 cc/g; BET specific surface area: 629 m$^2$/g; proportion of the pore volume of mesopore having a pore size of from 2 nm through 50 nm to the total pore volume is 42%), silica/alumina (SiO$_2$/Al$_2$O$_3$) mol ratio of which was 200, to obtain Y-type zeolite supported palladium-containing catalyst in which palladium metal was supported.

The reaction was carried out by using the catalyst obtained in the above in the same method as in Example 8 except that the reaction time was 38 minutes. As the result, the conversion of isobutylene was 75.2%, the selectivity to methacrolein was 49.9%, the selectivity to methacrylic acid was 19.0% and the productivity of methacrylic acid was 1.9 g/(g·h).

Comparative Example 4

The same method as in Example 8 was carried out except that a carrier to be used was changed to H-ZSM-5-type zeolite (total pore volume: 0.20 cc/g; BET specific surface area: 343 m$^2$/g; proportion of the pore volume of mesopore with a pore size of 2 nm to 50 nm to the total pore volume is 29%), silica/alumina (SiO$_2$/Al$_2$O$_3$) mol ratio of which was 485, to obtain H-ZSM-5-type zeolite supported palladium-containing catalyst in which palladium metal was supported.

The reaction was carried out by using the catalyst obtained in the above in the same method as in Example 8 except that the reaction time was 107 minutes. As the result, the conversion of isobutylene was 67.4%, the selectivity to methacrolein was 59.1%, the selectivity to methacrylic acid was 15.4% and the productivity of methacrylic acid was 0.5 g/(g·h).

A summary of the physical properties of the carriers used and the results of the reaction in Examples 8 and 9 and Comparative Example 4 are shown in Table 2. In Examples 8 and 9 where a carrier with a total pore volume of 0.40 to 1.50 cc/g was used, it was found that the selectivity to methacrylic acid and the productivity of methacrylic acid were good.

TABLE 2

| | Physical properties of carrier | | | | | | |
|---|---|---|---|---|---|---|---|
| | Total pore volume (cc/g) | Proportion of pore size of 2 to 50 nm (%) | Reaction time (min) | Selectivity to isobutylene (%) | Selectivity to methacrolein (%) | Selectivity to methacrylic acid (%) | Productivity of methacrylic acid (g/(g · h)) |
| Ex. 8 | 0.68 | 100 | 56 | 90.7 | 28.2 | 28.6 | 2.2 |
| Ex. 9 | 0.50 | 42 | 38 | 75.2 | 49.9 | 19.0 | 1.9 |
| Comp. Ex. 4 | 0.20 | 29 | 107 | 67.4 | 59.1 | 15.4 | 0.5 |

Example 10

Preparation of Catalyst

To 60 parts of 88% by weight n-valeric acid aqueous solution, 1.16 parts of palladium acetate was added and stirred under heating at 80° C. for 1 hour and dissolved. The resultant solution was introduced into an autoclave to which 5.4 parts of activated carbon made from raw coal (total pore volume: 0.43 cc/g; BET specific surface area: 840 m$^2$/g; proportion of the pore volume of mesopore having a pore size of from 2 nm through 50 nm to the total pore volume is 26%) was added. The system was stirred at a number of revolutions of 400 rpm, and inside of the autoclave was replaced by nitrogen by introducing and discharging nitrogen gas several times. Propylene gas was introduced into it to the pressure of 0.5 MPa and the resultant system was heated to 90° C. (reducing temperature) and kept at the same temperature for 1 hour (reducing time). After the reaction was finished, the system was cooled to 20° C., and the gas inside the autoclave was discharged and the autoclave was opened. The suspension was filtered and palladium-containing supported catalyst, the supported ratio of which was 10% by weight (the weight of palladium to the weight of carrier), was obtained.

The average particle diameter of palladium in the palladium-containing supported catalyst thus obtained was 1.5 nm (magnification of observation by transmission electron microscope: 1,000,000 fold).

(Evaluation of Reaction)

To the autoclave equipped with stirring device, 69 parts of 88% by weight acetic acid aqueous solution containing 200 ppm of p-metoxyphenol and 3 parts of the above-mentioned palladium-containing supported catalyst were introduced. Further, 2.5 parts of methacrolein was added. The autoclave was shut tight and stirring was carried out at a number of revolutions of 820 rpm, and the temperature was raised to 90° C. by heater. When the temperature reached 90° C., air was introduced into the autoclave to the internal pressure of 3.2 MPa, and the system was maintained in the same state for 20 minutes (reaction time). The amount of molecular oxygen used in the oxidation reaction was 0.77 mol to 1 mol of methacrolein. After the reaction was finished, the system was cooled to 20° C. To the gas outlet port of the autoclave, an absorption tube with cooled water inside and a gas sampling bag were attached in this order. The product gas was recovered by opening the gas outlet port and reducing the internal pressure of the reactor. The reaction liquid was transferred to a centrifuge tube and the catalyst was precipitated by centrifugation. The supernatant liquid was recovered by passing through membrane filter made of PTFE (pore size: 0.5 μm).

As the result, the conversion of methacrolein was 93.6%, the selectivity to methacrylic acid was 79.9%, the selectivity to a polymer/oligomer was 8.5% and the yield of methacrylic acid was 74.8%.

Example 11

The preparation of the catalyst was carried out in the same manner as in Example 10 except that an activated carbon made from raw coconut shell (total pore volume: 0.49 cc/g; BET specific surface area: 988 $m^2/g$; proportion of the pore volume of mesopore having a pore size of from 2 nm through 50 nm to the total pore volume: 10%) was used as a carrier. The average particle diameter of palladium in the palladium-containing supported catalyst thus obtained (the supported ratio of which was 10% by weight) was 2.6 nm (magnification of observation by transmission electron microscope: 300,000 fold).

The evaluation of the reaction was carried out in the same manner as in Example 10, and as the result, the conversion of methacrolein was 89.7%, the selectivity to methacrylic acid was 84.7%, the selectivity to a polymer/oligomer was 4.3% and the yield of methacrylic acid was 76.0%.

Comparative Example 5

The preparation of the catalyst was carried out in the same manner as in Example 10 except that 96% by weight of acetic acid aqueous solution was used as a solvent for preparation of catalyst. The average particle diameter of palladium in the palladium-containing supported catalyst thus obtained (the supported ratio of which was 10% by weight) was 8.4 nm (magnification of observation by transmission electron microscope: 300,000 fold).

The evaluation of the reaction was carried out in the same manner as in Example 10, and as the result, the conversion of methacrolein was 46.4%, the selectivity to methacrylic acid was 71.5%, the selectivity to a polymer/oligomer was 15.4% and the yield of methacrylic acid was 33.2%.

Comparative Example 6

The preparation of the catalyst was carried out in the same manner as in Example 10 except that n-valeric acid was used as a solvent for preparation of catalyst. The average particle diameter of palladium in the palladium-containing supported catalyst thus obtained (the supported ratio of which was 10% by weight) was 10.1 nm (magnification of observation by transmission electron microscope: 300,000 fold).

The evaluation of the reaction was carried out in the same manner as in Example 10, and as the result, the conversion of methacrolein was 45.4%, the selectivity to methacrylic acid was 65.2%, the selectivity to a polymer/oligomer was 21.3% and the yield of methacrylic acid was 30.0%.

Comparative Example 7

The preparation of the catalyst was carried out in the same manner as in Example 10 except that 0.11 parts of palladium acetate was used, reducing temperature was 25° C., and reducing time was 18 hours. The average particle diameter of palladium in the palladium-containing supported catalyst thus obtained (the supported ratio of which was 10% by weight) was 0.8 nm (magnification of observation by transmission electron microscope: 1,000,000 fold).

The evaluation of the reaction was carried out in the same manner as in Example 10 except that reaction time of methacrolein was 3 hours, and as the result, the conversion of methacrolein was 42.5%, the selectivity to methacrylic acid was 59.8%, the selectivity to a polymer/oligomer was 29.6% and the yield of methacrylic acid was 25.4%.

A summary of the average particle diameter of palladium in the catalysts used and the results of the reaction in Examples 10 and 11 and Comparative Examples 5 to 7 are shown in Table 3. In Examples 10 and 11 where a catalyst with an average particle diameter of palladium of 1 to 8 nm was used, it was found that the selectivity to methacrylic acid was high.

TABLE 3

| | Average particle diameter of palladium (nm) | Conversion of methacrolein (%) | Selectivity to methacrylic acid (%) | Selectivity to polymer/oligomer (%) | Yield of methacrylic acid (%) |
|---|---|---|---|---|---|
| Ex. 10 | 1.5 | 93.6 | 79.9 | 8.5 | 74.8 |
| Ex. 11 | 2.6 | 89.7 | 84.7 | 4.3 | 76.0 |
| Comp. Ex. 5 | 8.4 | 46.4 | 71.5 | 15.4 | 33.2 |
| Comp. Ex. 6 | 10.1 | 45.4 | 65.2 | 21.3 | 30.0 |
| Comp. Ex. 7 | 0.8 | 42.5 | 59.8 | 29.6 | 25.4 |

As mentioned above, by using the catalyst of the present invention, an α,β-unsaturated carboxylic acid can be produced through liquid-phase oxidation of an olefin or an α,β-unsaturated aldehyde in good reaction performance.

What is claimed is:

1. A method for producing an α,β-unsaturated carboxylic acid through liquid-phase oxidation of an olefin or an α,β-unsaturated aldehyde with molecular oxygen in the presence of a catalyst in a dispersed state in a reaction liquid, wherein the catalyst comprises palladium supported on a carrier with a total pore volume of 0.40 to 1.50 cc/g as measured by nitrogen gas adsorption method.

2. The method according to claim 1, wherein the total pore volume of the carrier as measured by nitrogen gas adsorption method is 0.40 to 0.80 cc/g.

3. The method according to claim 2, wherein a proportion of the pore volume of the mesopore having a pore size of from 2 nm through 50 nm of the carrier as measured by nitrogen gas adsorption method to the total pore volume of the carrier is 40% or less.

4. The method according to claim 1, wherein the total pore volume of the carrier as measured by nitrogen gas adsorption method is 0.80 to 1.50 cc/g.

5. The method according to claim 4, wherein a proportion of the pore volume of the mesopore having a pore size of from 2 nm through 50 nm of the carrier as measured by nitrogen gas adsorption method to the total pore volume of the carrier is 10% or less.

6. A method for producing an $\alpha,\beta$-unsaturated carboxylic acid through liquid-phase oxidation of an olefin or an $\alpha,\beta$-unsaturated aldehyde with molecular oxygen in the presence of a catalysts in a dispersed state in a reaction liquid, wherein the catalyst comprises palladium with an average particle diameter in the range of 1 to 8 nm supported on a carrier.

* * * * *